(12) United States Patent
Vaisnys et al.

(10) Patent No.: US 8,489,207 B1
(45) Date of Patent: Jul. 16, 2013

(54) MEDICAL DEVICE WITH USER ATTENTION DIRECTION

(76) Inventors: Gintaras A Vaisnys, Chicago, IL (US); Glenn W. Laub, Princeton, NJ (US); Giovanni C Meier, Madison, CT (US)

( * ) Notice: Subject to any disclaimer, the term of this patent is extended or adjusted under 35 U.S.C. 154(b) by 515 days.

(21) Appl. No.: 12/655,750

(22) Filed: Jan. 5, 2010

(51) Int. Cl.
*A61N 1/39* (2006.01)

(52) U.S. Cl.
USPC ............ 607/142; 607/1; 607/2; 607/5; 607/9; 607/10; 607/11; 607/14; 607/15; 607/16; 607/17; 607/18; 607/27; 607/28; 607/29; 607/30; 607/31; 607/32; 607/33; 607/36; 607/37; 607/38; 607/115; 607/149; 607/152

(58) Field of Classification Search
USPC ................... 607/1–2, 5, 9–11, 14–18, 27–33, 607/36–38, 115, 142, 149, 152
See application file for complete search history.

(56) References Cited

U.S. PATENT DOCUMENTS

| 6,694,193 B2 * | 2/2004 | Lyster et al. ................... 607/142 |
| 2005/0131465 A1 * | 6/2005 | Freeman et al. ................... 607/5 |

* cited by examiner

*Primary Examiner* — Deborah Malamud
(74) *Attorney, Agent, or Firm* — William B. Gowanlock

(57) ABSTRACT

A medical device having a unit in communication with ancillary components wherein the unit and the ancillary components each have a sensory output through which communication with a user of the medical device may be accomplished and to which the user's attention directed. In one aspect, the medical device is an AED unit with associated pads, which are an ancillary component electrically connected to the AED unit. In this illustrative example, the unit has a unit sensory output (e.g., a speaker or a display), and the pads, and/or their associated packaging, have an ancillary sensory output (e.g. a speaker or display). Programming in the AED unit controls output to the sensory outputs such that the user's attention is directed between the unit and the ancillary components.

1 Claim, 7 Drawing Sheets

AED MAIN STEPS
(Selective Portion)

MEDICAL DEVICE WITH USER ATTENTION DIRECTION

TECHNICAL FIELD

The present invention relates to medical devices, and, more specifically, to medical devices using integral ancillary components, such as AEDs using pads, wherein the unit and the ancillary component each have a sensory output (e.g., a display).

BACKGROUND OF THE INVENTION

External defibrillators are emergency medical devices designed to supply a controlled electric shock (i.e., therapy) to a person's (e.g., victim's) heart during cardiac arrest. This electric shock is delivered through the pads that are electrically connected with the external defibrillator and in contact with the person's body.

To provide a timelier rescue attempt for a person experiencing cardiac arrest, some external defibrillators have been made portable, by utilizing battery power (or other self-contained power supplies). In addition, many portable external defibrillators have programming to make medical decisions making possible operation by non-medical personnel.

These portable external defibrillators, commonly known as automated external defibrillators (AEDs), including automatic and semi-automatic, have gained acceptance by those outside the medical profession and have been deployed in myriad locations outside of traditional medical settings. Due to the life saving benefits of AEDs, more and more AED are being purchased and deployed in public areas for use by the public. This allows for a rescue attempt without the delay associated with bringing the person to a medical facility, or bringing a medical facility to the person (e.g., a life support ambulance).

Individuals as well as businesses are purchasing and deploying AEDs. As time is of the essence during any rescue attempt, multiple AEDs may be purchased by any particular individual or user to allow placement at multiple locations. In the case of an individual, this could be on several floors of a home, and in the case of a business, this could be for placement throughout a facility (e.g., factory, office building, or large retail center). Thus, regardless of where the victim is within the home/facility, access to an AED would only be seconds, or minutes, away.

As indicated above, it is anticipated that many AEDs will be operated in a rescue attempt by members of the public who have none or minimal training, but none to minimal practical experience. In order to enhance the chances of a successful rescue attempt, these users will need assistance. In all likelihood, this assistance will come from the AED, in the form of instructions. Presently, AEDs incorporate both visual and audio systems to deliver instructions to a user.

The problem with present methods of delivering instructions is that the user's attention is diverted from the victim to the AED unit. More specifically, when an AED is used in a rescue attempt, a user typically is required to focus on the victim, but receives instructions from the AED unit. As a result, the user's attention is constantly being directed back to the AED unit even though the user's attention at that moment should be focused elsewhere. What is needed in the art is a better method to delivering instructions to a user, such that the user's attention is properly directed.

Furthermore, other desirable features and characteristics of the present invention will become apparent for the subsequent detailed description of the invention and the appended claims, taken in conjunction with the accompanying drawings and this background of the invention.

SUMMARY OF THE INVENTION

The invention is a medical device having a unit in communication with ancillary components wherein the unit and the ancillary components each have a sensory output through which communication with a user of the medical device may be accomplished and the user's attention directed.

In one aspect, the medical device is an AED unit with associated pads, which are an ancillary component electrically connected to the AED unit. In this illustrative example, the unit has a unit sensory output (e.g., a speaker or a display), and the pads, and/or their associated packaging, have an ancillary sensory output (e.g. a speaker or display). Programming in the AED unit controls output to the sensory outputs such that the user's attention is directed between the unit and the ancillary components.

Other features, attainments, and advantages will become apparent to those skilled in the art upon a reading of the description when taken in conjunction with the accompanying drawings.

DETAILED DESCRIPTION OF EXEMPLARY EMBODIMENTS

Figure 1:
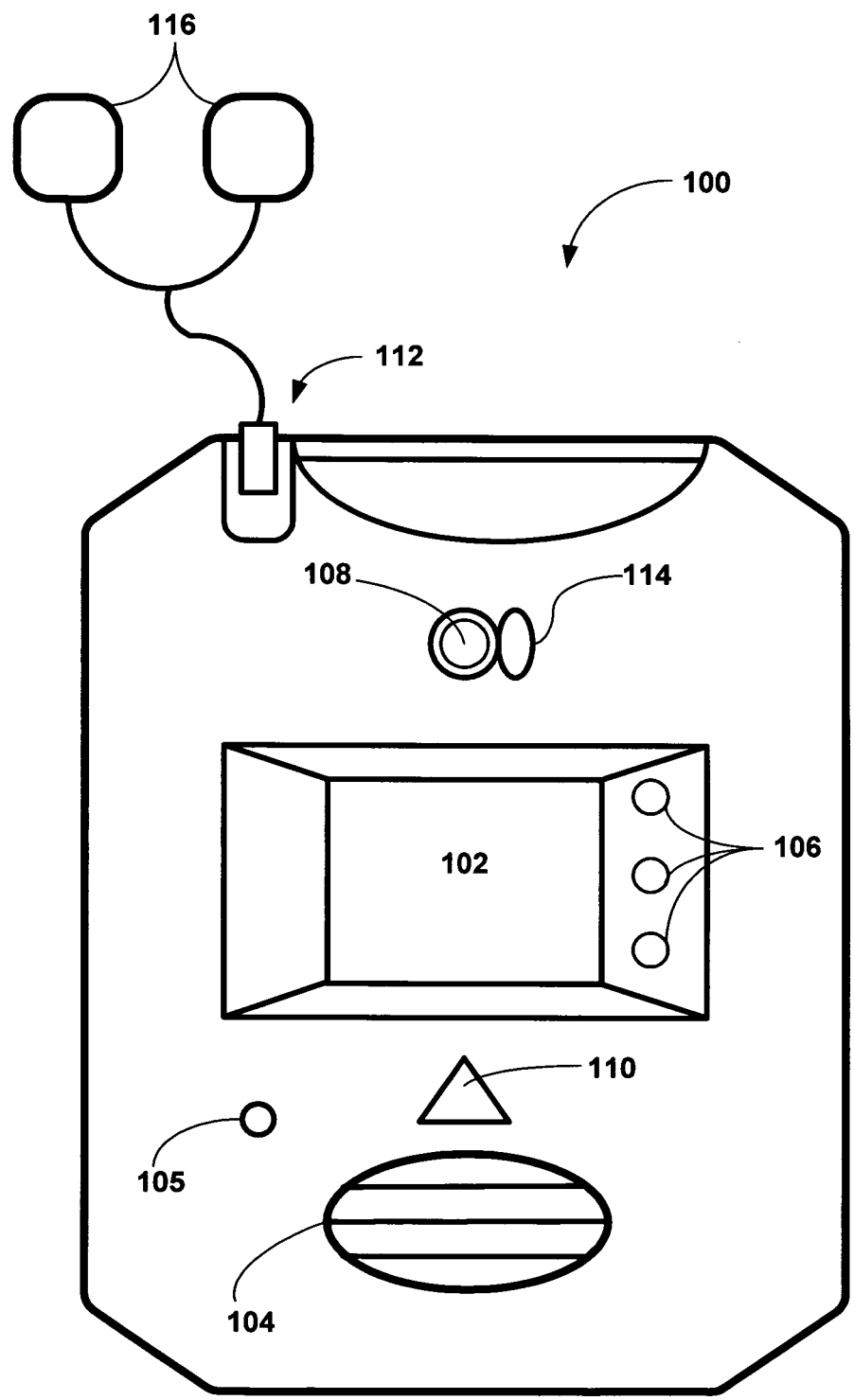
FIG. 1 is a top view of an illustrative AED on which the present invention may be used.

Turning now to the drawings, FIG. 1 illustrates a plan view of an AED unit 100. As seen in this FIG. 1, the AED unit 100 has sensory outputs (i.e., a video display 102, a speaker 104), an audio output jack 105, and a user interface 106. The AED unit 100 further includes an ON/OFF switch 108, a shock switch 110, a ancillary connector 112, and an active status indicator 114 (e.g., a light source which blinks green indicating in OFF sub-mode and operating normally, solid green indicating in ON mode and operating normally, solid red indicating in ON mode with a problem, and blinking red indicating in OFF sub-mode with a problem).

The ancillary connector 112 connects an ancillary component 116, in this case pads, to the AED unit 100. Ancillary components 116, such as pads, are an integral ancillary component. More specifically, the pads are required for the AED unit 100 to be used. In a rescue attempt, the pads connect a victim to the AED unit 100, thereby permitting the AED unit to deliver a shock to a victim.

Figure 2:
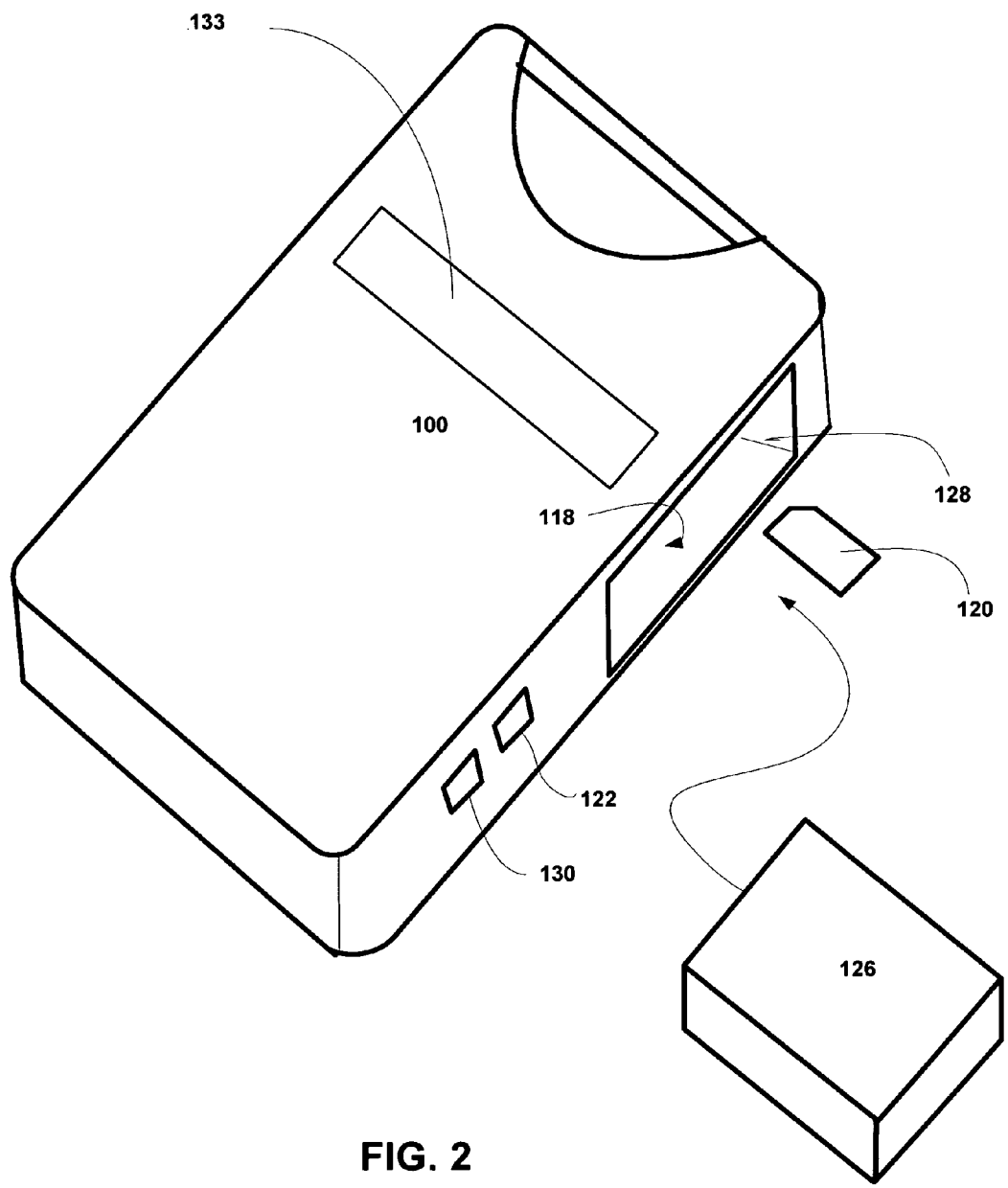
FIG. 2 is a perspective side view of the AED depicted in FIG. 1.

Referring to FIG. 2, the AED unit 100 further includes a card port 118 (not visible) for providing an electronic interface for a card 120. The card 120 illustrated is a secure digital card (commonly referred to as SD card), but other removable memory devices (e.g., card ports and types), well known to those skilled in the art, could be used. It is possible the card 120 may not be required for the AED unit 100 to perform its medical procedure, as the card may be used as a data recorder.

Additionally, the AED unit 100 further includes a standardized interface socket 122, e.g., universal serial bus (more commonly known as a USB port). Depending upon programming, the standardized interface socket 122 can permit the AED unit 100 to interface with any number of devices, such as a keyboard and/or mouse 124, or a mass storage device 125 (see FIG. 3). As those skilled in the art will appreciate, other devices, such as a computer, could be connected using a universal serial bus.

Further, the AED unit 100 includes a battery 126 (removed from AED unit for clarity) that provides the main power. While an internal battery could be used, the illustrated battery 126 slides into a battery slot 128 in which the battery may be secured permanently (i.e., non-user removable) or removably (i.e., user removable). Where the battery 126 is removably secured in the battery slot 128, a faulty battery can generally be replaced by a user. It should be appreciated that the AED unit 100 could also be powered by connection to a power grid (e.g., a typical 120 v outlet) (not shown), but portability of the AED results from the ability of the device to function exclusively on battery power. In addition, an ability to recharge the battery 126 could be provided (not shown). The implementation of power from a power grid and battery 126 recharge capabilities are well known to those skilled in the art.

It should be appreciated that the card port 118, as illustrated, is located inside the battery slot 128. As a result, the battery 126 must be removed to insert or remove the card 120 from the card port 118. It is certainly possible to relocate the card port 118 to provide easier access to insert and remove the card 120 from the card port.

Additionally, the AED unit 100 may include a network interface 130. The network interface 130 may permit the AED unit 100 to communicate with another computer 132 (see FIG. 3), such as by an intranet, an internet, or pier-to-pier. The network interface 130, while illustrated as wired, could be wireless, optical, or otherwise. Common network interfaces include a 10/100 network connection, infrared (IR), firewire and Wi-Fi. Those skilled in the computer networking arts are familiar with programming and implementing these types of network interfaces.

Further, the AED unit 100 may have an ancillary component slot 133. The ancillary component slot 133 stores the ancillary component 116. It should be appreciated that ancillary component 116 in the case of an AED is most likely a pad pouch (discussed below) for protection of the pads from the environment. Further, the ancillary component slot 133 can be dimensioned to hold all or just some portion of the ancillary component 116. Where the ancillary component 116 is merely placed in the ancillary component slot 133, the dimensions of the pad slot should be sufficient to hold the ancillary component 116 such that it can be moved with the AED unit 100.

Figure 3:
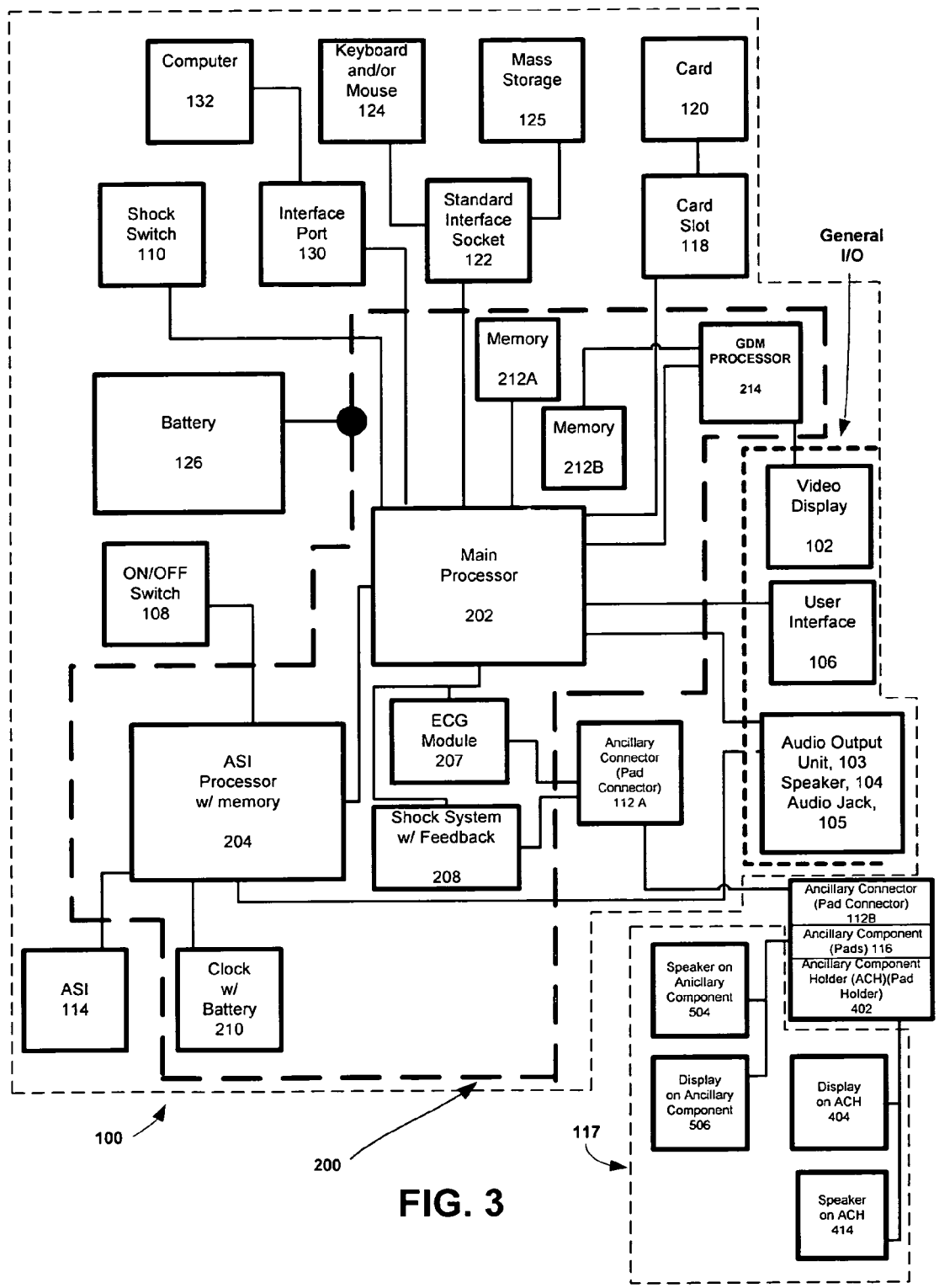
FIG. 3 is a functional block diagram of the components of the AED depicted in FIGS. 1 and 2.

FIG. 3 is a functional block diagram AED unit 100. In addition, FIG. 3 also shows the interface of the AED unit 100 with various accessory components discussed above, such as the ancillary component 116, another computer 132, a keyboard and/or mouse 124, and a mass storage device 125.

The AED unit's 100 circuitry (collectively referred to by reference number 200) includes a main processor 202, an active status indicator (ASI) processor 204, an ECG module 207 for receiving and conditioning ECG signals received using the ancillary component 116 (e.g., the pads 116), a shock system with feedback 208, and a GDM processor 214, which are all powered by the battery 126. The main processor 202, ASI processor 204, and GDM processor 214 include programmable circuitry, for running programs, including control programming, stored in memories 212A and B. As those skilled in the art of computer circuitry design will appreciate circuit design alternatives are numerous, thus the present invention should not be considered limited by this exemplary circuitry.

Where the ancillary component 116 is a single use item, the ancillary component 116 is temporarily connected to the AED unit 100 by an ancillary connector 112A, B (two cooperating parts, such as male and female portions, that form a temporary electrical connection). The ancillary component 116 is electrically connected to the shock system 208 and the main processor 202. The electrical connection for the ancillary component 116 with the shock system 208 permits an electrical discharge within the AED unit 100 to be transmitted to a victim. The electrical connection to the pads from the main processor 202 allows content generated within the AED unit, to be transmitted to a sensory output 117. It should be appreciated that various drivers (not shown) may be needed to convert the content from the main processor 202 into a usable form for the sensory output 117.

The AED unit 100 has two primary modes—OFF and ON. The OFF mode, sometimes referred to as an OFF mode, has several sub-modes including SELF-TEST and AUXILIARY. The OFF-SELF-TEST sub-mode is the default mode. More specifically, the AED unit 100 must always be in a mode. Thus, when the AED unit 100 is referred to as being in the OFF mode, it is in one of the sub-modes. For a user, the ON mode, which is activated by the ON/OFF switch 108, means that the AED unit 100 has been activated to perform a rescue.

In the OFF SELF-TEST sub-mode, the circuitry 200 of the AED unit 100 utilizes minimal power to maintain basic functions of the AED such as running a clock 210 (which is shown as having a backup battery) and automatically (i.e., without human intervention) initiating self-tests, so that scheduled self-diagnostic maintenance checks in response to the passage of time are performed.

Generally, for a rescue attempt, the AED unit 100 is put into the ON mode from the OFF SELF-TEST sub-mode by operation of the ON/OFF switch 108. After the rescue attempt, the AED unit 100 may be put back into the OFF SELF-TEST sub-mode by operation of the ON/OFF switch 108. The AED unit 100 may contain programming to put it back into the OFF SELF-TEST sub-mode automatically.

The main processor 202 is capable of executing computer programming, stored in memory 212A, and primarily controls the AED unit 100 in the ON and OFF sub-modes, excluding the OFF SELF-TEST sub-mode. The ASI processor 204 is also capable of executing computer programming stored in memory 212B and primarily controls the AED unit 100 in the OFF SELF-TEST sub-mode, but does perform self-tests by awaking the main processor 202 which determines the necessary self-test and retrieves and runs the applicable computer programming. The ASI processor 204, however, provides backup to the main processor 202 in the event of a failure of the self-test programming that should have run on the main processor. In other words, both the main processor 202 and the ASI processor 204 are capable of controlling the output displayed via the active status indicator 114.

In the ON mode, unlike the OFF sub-modes, the AED unit 100 circuitry 200 is capable of delivering a shock via the ancillary component 116 to a patient. For example, the main processor 202 controls the shock system 208. In the ON mode, the shock system 208 is charged and then may be discharged through the ancillary component 116, if appropriate, as a result of pressing the shock switch 110. If a shock is deemed inappropriate, the shock system 208 is capable of being internally discharged. When the ON mode is entered, the circuitry 200, however, may be checked by a self-test.

The OFF AUXILIARY sub-mode may be manually entered using the user interface 106. This is discussed below in detail.

The video display 102, which is driven by drivers running on the GDM processor 214, should be capable of displaying images, such as text, pictures, or combination, stored in a video format (i.e., captured in frames). As illustrated, the video display 102 is an integrated component of the AED unit 100.

The video display 102 is a display ideally capable of pixel, or equivalent, addressing. Well known types of displays that meet this requirement are liquid crystal displays (LCD), plasma displays, projection displays and cathode ray tubes (CRT). Depending upon the requirements of the specific application, the video display 102 may be black and white, gray scale or color.

The video display 102 may perform multiple functions depending upon the mode. For example, the video display 102 in the ON mode may display information related to performing a rescue attempt to guide a user through the procedure. When in the OFF AUXILIARY sub-mode, the video display 102 may allow a user to select and to run desired programming, which is discussed below. More specifically, the user interface 106 may be used to enter the OFF AUXILIARY sub-mode, which in turn starts a graphical user interface (GUI) on the video display 102.

Through selections made on the GUI, the AED unit 100 when in the OFF AUXILIARY sub-mode may be put into the ON mode, or back into the OFF SELF-TEST sub-mode. Normally, the AED unit 100 defaults to the OFF SELF-TEST sub-mode by merely exiting the OFF AUXILIARY sub-mode, when the proper option selection on the user interface 106 is made. However, in an emergency, the ON/OFF switch 108 could activate programming upon operation (OFF to ON) (e.g., act as an interrupt) that terminates the OFF AUXILIARY sub-mode and puts the AED unit 100 in the ON mode. In the alternative, the GUI interface could display an option which upon selection using the user interface 106 switches the AED unit 100 from the OFF AUXILIARY sub-mode to the ON mode.

When in the OFF AUXILIARY sub-mode, the AED unit 100 has control programming that permits a user to navigate through the various programs, or information, to which the AED unit has access. For example, a menu may be presented on the video display 102 that allows a user to select from such options as VIEW UNIT INFORMATION, MAINTENANCE MENU, TRAINING MENU, and HELP. Generally, options are arranged in a hierarchal order. Therefore, selection of an option could activate, or start, a program to which the AED unit 100 has access, such as in memory 212A, or it could result in another menu from which further selections could be made.

In order to use the GUI, users interact with the AED unit 100 by using the user interface 106 to respond to or select options displayed on the video display 102 or entering data into the AED unit. A rudimentary user interface 106 having three push-buttons is illustrated (see FIG. 1).

This type of interface is most effective when the video display 102 is programmed to display a series of displays wherein each display contains selectable options. More specifically, the video display 102 is activated (e.g., enters the OFF AUXILIARY sub-mode) by pressing one of the switches of the user interface 106 that in turn presents one or more options on the video display. A user then scrolls generally sequentially through the options using one switch for up and another for down placing a cursor on an option. When the cursor is on the desired option, the user selects the option by pressing the third switch. Typically, the three switches will be presented to the user with the two scroll switches having the select switch in between.

It should be appreciated that this is but one user interface. An example of a more sophisticated user interface is the keyboard (e.g., QWERTY) and/or mouse 124.

In addition, the video display 102 could have the user interface 106 incorporated. More specifically, the video display 102 could be an interactive display, such as a touch display (e.g., touch screen) or display that interacts with a light pen. As those skilled in the art of computer circuitry design will appreciate, where an interactive display replaces an output only type display, the need for additional user interfaces, such as a keyboard or a mouse, is minimized, or eliminated.

While the user interface in the interactive display may mimic the user interface 106 discussed above, it may be enhanced. More specifically using the example of a touch display, option selections could be made directly without scrolling and data could be entered using an on-display keyboard, or even direct handwriting.

It should be appreciated that the above-discussed user interfaces are not an exclusive list and one need not be used to the exclusion of another. As those skilled in the art will appreciate, multiple user interfaces may be used simultaneously.

The speaker 104 and audio output jack 105 are part of the audio in/out. The speaker 104 may be used for presenting audible information, such as instructions using words, or alerts using sounds, or it may act as a microphone to allow audible information, such as speaking, to be recorded into memory, such as the memory 212. The speaker 104 in the OFF SELF-TEST sub-mode may be used to provide a sound, such as a chirp, to indicate that maintenance of the AED unit 100 is required.

As described above, the ON/OFF switch 108 may be operated by a user to switch the AED unit 100 between OFF (i.e., OFF SELF-TEST sub-mode) and the ON mode. When the AED unit 100 is in its ON mode, the ancillary component 116, which maybe attached to the AED unit 100 via the ancillary connector 112, may be used to monitor ECG information from a patient to determine if the patient's cardiac rhythm is suitable for defibrillation shock, or whether the rhythm is a non-shockable rhythm. The ancillary component 116 acquires patient data that is transmitted to the main processor 202, via the ECG module 207. The main processor 202 has programming suitable for analyzing the data to determine if a shockable rhythm is present. The programming and the parameters to determine a shockable rhythm are known to those skilled in the defibrillator art.

The main processor 202 has operational programming that permits the AED unit 100 to perform its medical procedure, such as in the case of an AED defibrillation. For an AED, this operational programming may include procedures for evaluating whether a victim has a shockable rhythm and for properly charging the shock system 208 to deliver a proper shock. Operational programming for AEDs is well known in the art.

As indicated above, the AED unit 100 is generally put into the ON mode by a user pushing the ON/OFF switch 108. After entering the ON mode, the AED unit 100, in addition to running basic programming needed to perform its medical purpose (e.g., heart rhythm analysis to determine a shockable rhythm and developing a shock potential), may have additional programming, such as assistance programming (e.g., coaching program, to provide assistance to the user in performing a rescue attempt). Programming for use in a rescue attempt is generally stored in memory 212.

Figure 4:
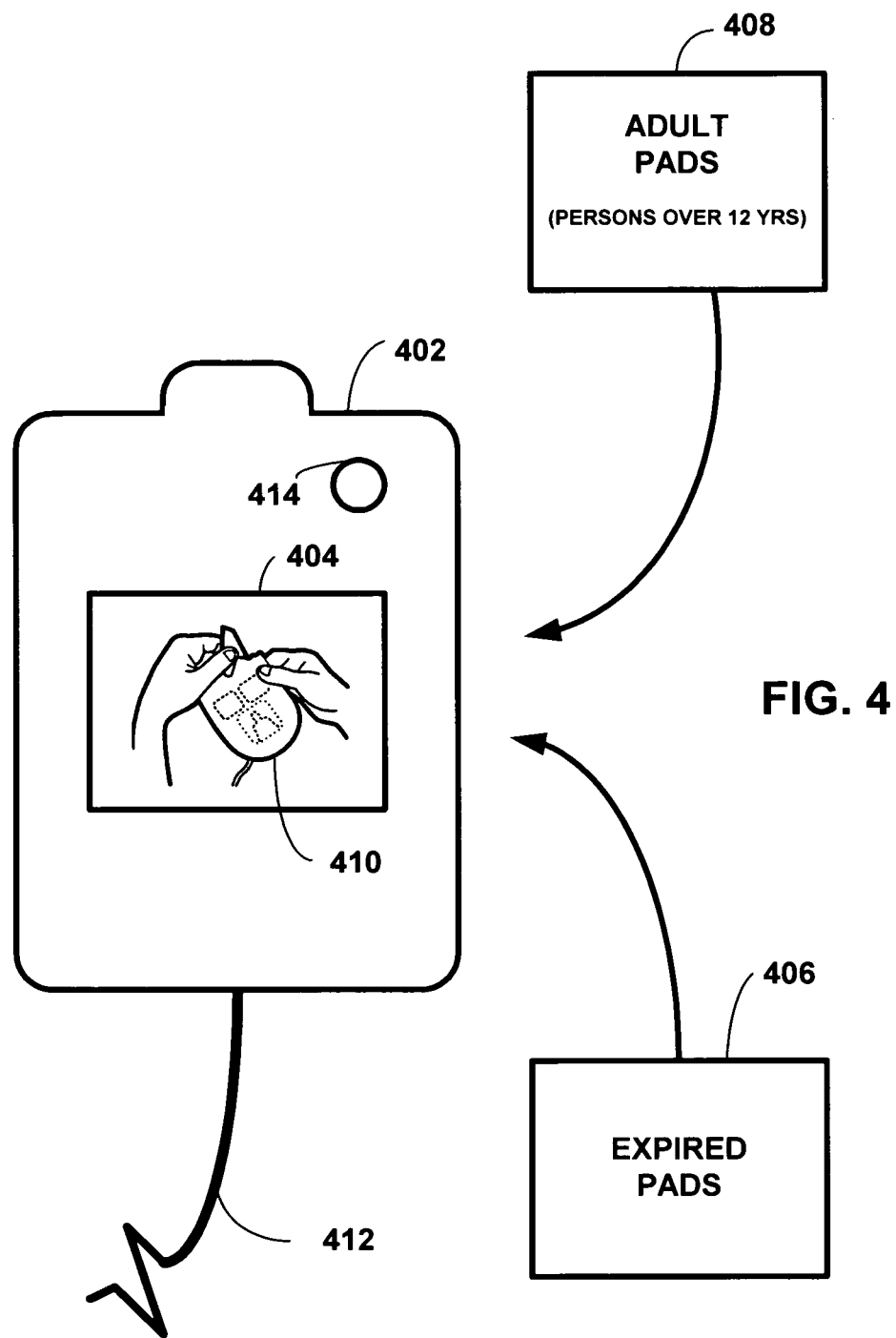
FIG. 4 is illustration of an ancillary component holder having a display thereon, with alternative content for display on the display.

As shown in FIG. 4, the ancillary component 116, such as pads which can be crumpled, may be stored in an ancillary component holder 402, such as a pad holder. The ancillary component holder 402 protects the ancillary component 116, primarily from environmental degradation. In the case of pads, the pads may be hermetically sealed inside the pad holder.

Figure 5:
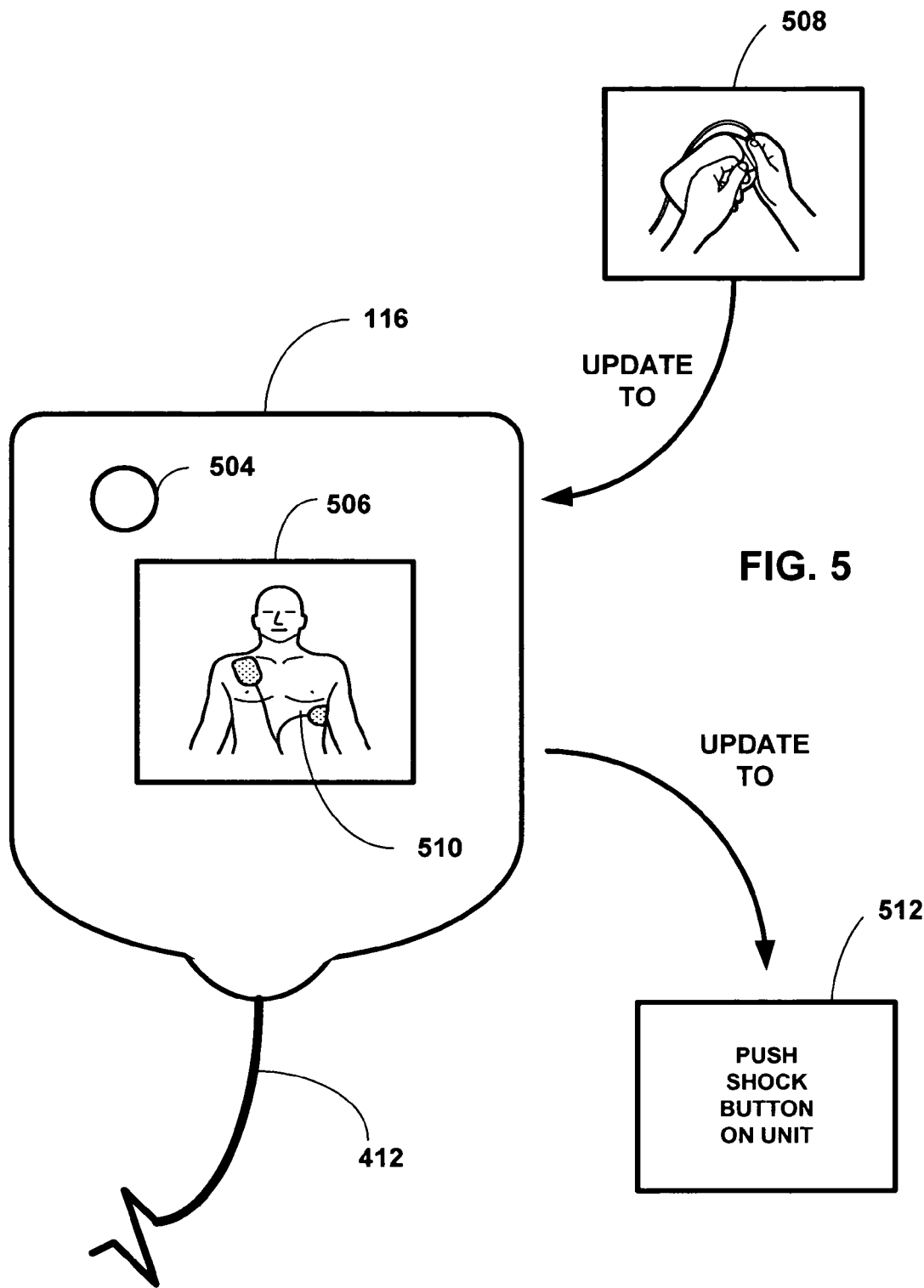
FIG. 5 is an illustration of a pad having a display thereon, with alternative content for display on the display.

The ancillary component 116 is connected to the AED unit 100 by a cable 412 (see FIG. 5). The cable 412 connects to the AED unit 100 using an ancillary connector (see FIGS. 1 and 3).

The ancillary component holder 402 may have sensory outputs. More specifically, the ancillary component holder 402 may have a display 404 for displaying one or more images 406, 408, and 410. Image updates may be provided from the AED unit 100 via a cable 412. The ancillary component holder 402 may have a speaker 414.

In addition to or in the alternative, the ancillary component holder 402 may have an audio output 414, such as a speaker, which would be in communication with the AED unit 100 via the cable 412.

The cable 412 may have multi-conductors. More specifically, as indicated above, the cable 412 connects the ancillary component 116 to the AED unit 100, but it may also contain wiring to support the display 404 and the speaker 414. Where the cable 412 is a single multi-strand cable, the interface for all the strands with the AED unit 100 should be through a single ancillary connector 112. If the cable 412 is merely a composite of multi-cables (e.g., one for the pads, one for the speaker and one for the display), the cables should be connected to the AED unit 100 using one or more temporary connectors, such as plug and socket connectors, so that the ancillary component 116 can be easily replaced. As those skilled in the art will appreciate, data can be transmitted in many ways, for example wirelessly or using a single wire with mixed data, therefore the foregoing should be considered illustrative only.

As shown in FIG. 5, the ancillary component 116 may also have sensory outputs. More specifically, the ancillary component 116 may also have a display 506 and/or a speaker 504.

Connection of the display 506 and/or speaker 504 is the same as that described above for display 404 and speaker 414 associated with the ancillary component holder 402.

The ancillary component 116, in the case of an AED pads, are generally only viewed during a rescue attempt when they are removed from the ancillary component holder 402 (e.g., a pad holder), the content on the display 506 will generally contain instructional material. As illustrated typical content could include an illustration as to removal of a backing 508 on the ancillary component 116, which exposes the adhesive and gel, then after that is accomplished updating to content on the display 506 to show where to place the pads on a victim 510, and then determine if the pads are properly attached.

Where the ancillary component 116 and/or ancillary component holder 402, is flexible, a suitable display should also be flexible. In the case of pads used with an AED, a flexible display will allow proper placement of the pads on a victim. More precisely, when the ancillary components 116 are pads, the pads are flexible so that they will contour to the surface on which they are being placed.

Flexible displays can be serially addressable or optically addressable. The images are extremely stable and can even be retained if power is lost, or the driving electronics are decoupled. Where the display is an optically addressed ChLCD, an image, which was created on the display by optical addressing, is exposed. More specifically, a single pulse at a single voltage is applied to the display exposing the image. Thus, the display can appear blank (i.e., "off") and then on queue display content (I.e., "on"). It should be appreciated if an optically addressed display is used, updating of the display after installation on the ancillary device is not practical.

It should be appreciated that automatic updating (i.e., updating done without user intervention) of content on a display requires that the AED have some mechanism for determining when to update the content. In certain cases, the AED could have the sensors with associated programming to recognize when an event has been accomplished, thus updating should occur. In other cases, updating could occur merely as a result of the passage of time. The sensors and programming to accomplish either mechanism is well known to those skilled in the art. Generally, the type of content and the updating of that content will be directly related to the assistance programming provided by the AED unit 100.

It should be appreciated where there are multiple ancillary components 116 or auxiliary component holders 402, each could have an output device, such as a display or speaker.

When the AED unit 100 is turned ON, by pushing the ON/OFF button 108 to affect a rescue attempt the AED unit has programming to assist the user. More specifically, programming in the AED unit is designed to instruct the user on the steps necessary to perform a rescue attempt. These instructions are provided in an intelligible form, such as words, phrases, or diagrams, depending upon the capabilities of the AED unit.

Figure 6:
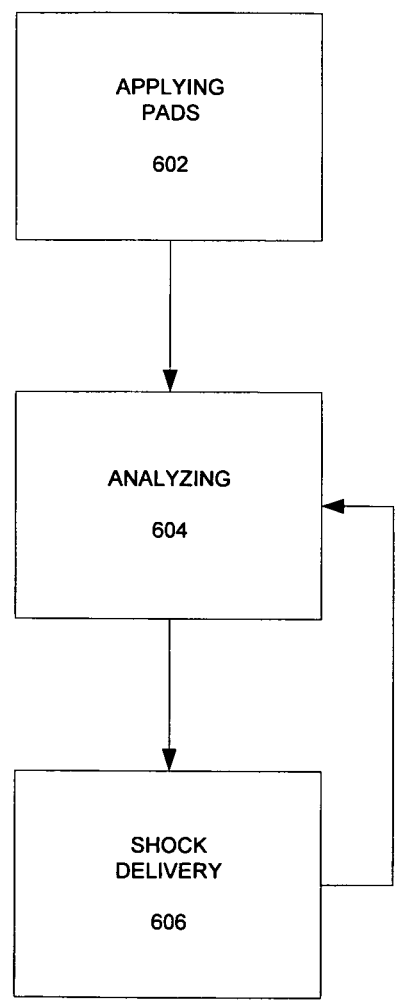
FIG. 6 is a logic flow diagram of a selective portion of some main steps an AED uses to provide assistance to a user in a rescue attempt.

A representative portion of a sequence of instructions for providing user assistance is shown in FIG. 6. This illustrated portion of AED user assistance programming has three main steps—applying pads 602, analyzing the victim's heart rhythm to determine if there is a shockable rhythm 604, and shock delivery 606, if appropriate. The AED unit might also inform the user when it is time to perform certain functions, such as performing CPR and when not to touch the victim (e.g., when the AED is analyzing the victim's heart rhythm to determine if a shockable rhythm is present).

Figure 7:
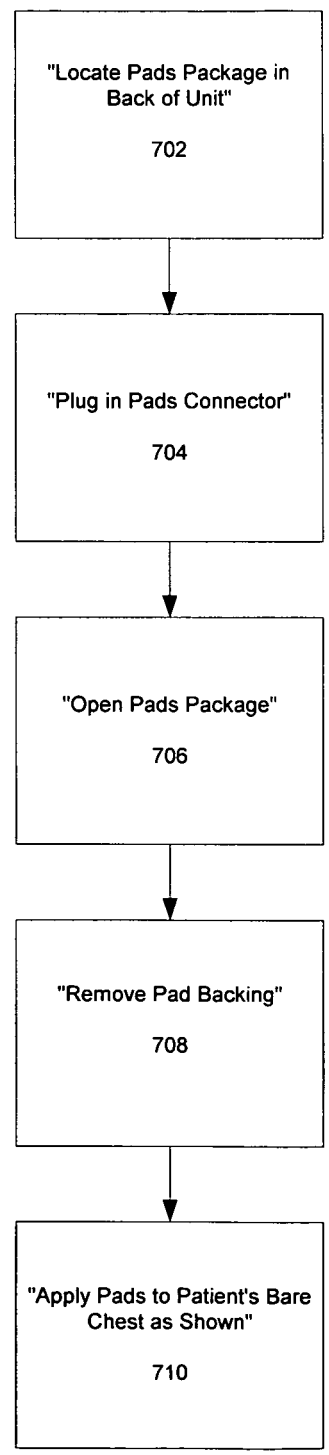
FIG. 7 is a logic flow diagram of sub-steps that may be contained in the step of applying the pads, shown in FIG. 6.

As shown in FIG. 7, the main step of apply pads to a victim has the five sub-steps of—locating the pads package in the back of the AED unit 702, plugging in pads connector 704, opening the pads package to gain access to the pads 706, remove the pad's protective backing 708, and applying the pads to patient's bare chest 710. As those skilled in the art will appreciate, depending upon feedback circuits that the AED unit 100 may have to determine its present status, certain sub-steps may be omitted or repeated. For example, if the AED unit 100 can determine that the pads connector is plugged in, the sub-step directing the plugging in of the pads connector may be omitted. Alternatively, if the pads are expired and the programming of the AED can determine this, a sub-step instructing the user to replace the pads with new pads might be added.

Using the illustrated sub-steps associated with applying the pads, user attention direction will be illustrated. User attention direction is based on the AED providing guidance to the user through various techniques on where the user's attention should be focused. For example, should the user be interacting with the AED unit 100 or the victim.

The degree and type of direction that the AED can provide depends on the capabilities of the AED unit 100, the ancillary component 116, and the ancillary component holder 402. The illustrative AED described above has an AED unit 100 having a display 102 and a speaker 104, an ancillary component 116 having a display 506 and a speaker 504, and an ancillary component holder 402 having a display 404 and a speaker 414. It should therefore be appreciate that a lesser equipped AED may require modification of the method.

Beginning with the first sub-step—locating the pads package in back of unit, this instruction could be given from the AED unit 100 speaker 104. It could also be given on the AED unit 100 display 102. This would direct the user's attention to the AED unit 100.

The next step, if needed,—plug in pads connector, could also be given by the AED unit's speaker 104 and/or display 102. This would keep the user's attention focused on the AED unit.

The next sub-step—open pads package, would be given by the pad package's speaker 414 and/or display 404. This would direct the user's attention to the pads package and away from the AED unit 100. At this time, the pad package's display 404 could show an illustration as to how the pad package is to be opened. (see FIG. 4).

The next sub-step—remove pad backing, could be given by the pad's speaker 504 and/or display 506. This would direct a user's attention to the ancillary component 116. At this time, the display 506 could illustrate how to remove the backing. (see FIG. 5).

The next sub-step—apply pads to patient's bare chest as shown could be given by the pad's speaker 504 and/or display 506. This would tend to keep the user's attention directed at the pads.

It should be appreciated that a command may be similarly given from the speaker and display, or given differently. More specifically, a speaker may give the command while a display might give a picture of the intended outcome, as shown in FIG. 5 and identified by reference number 510. This figure could be associated with the sub-step command of apply pads to patient's bare chest.

While the above illustrative example has relied on sound to redirect the attention of a user, other redirecting procedures could be used. For example, the messages on the various displays could be used. As shown in FIG. 5, the display 506 could give the message PUSH SHOCK BUTTON ON UNIT. This command would redirect the user's attention from the victim back to the AED unit 100.

It should be appreciated that when there are several speakers and several displays, numerous combinations of command presentations could be used to redirect constantly a user's attention.

It should also be appreciated that the commands given do not necessarily need to be intelligible (e.g., words, phrases, or pictures). For example, beeps could be used. For example, in the case where both the unit and the ancillary component both have a speaker, the beep would originate from the item to which a user's attention should be directed.

This same strategy could be applied for a display. The display could flash or have a flashing character, such as an exclamation point. Alternatively, a message on one display could direct the user's attention somewhere else, such as from the pads to the unit.

The programming required herein is within those skilled in the art based upon the descriptions provided. More specifically, programming of AEDs is well known in the art, as is programming of instructional material on AEDs related to assisting a user in a rescue attempt.

Alternative embodiments of the invention will become apparent to one of ordinary skill in the art to which the present invention pertains without departing from its spirit and scope. Thus, although this invention has been described in exemplary form with a certain degree of particularity, it should be understood that the present disclosure has been made only by way of example and that numerous changes in the details of the construction and the combination and arrangement of parts or steps may be resorted to without departing from the spirit or scope of the invention. Accordingly, the scope of the present invention is defined by the appended claims rather than the foregoing description.

What is claimed is:

1. An AED comprising:
   an AED having a set of pads attached thereto,
   wherein the pads have mounted thereto an ancillary intelligent user output;
   wherein at least one of pads of the set of pads is stored in a pad holder, and the pad holder has mounted thereto an ancillary intelligent user output; and
   wherein the ancillary intelligent user output is selected from the group consisting of a video display and a speaker.

* * * * *